United States Patent [19]

Wolfbeis et al.

[11] Patent Number: 4,580,059

[45] Date of Patent: Apr. 1, 1986

[54] METHOD FOR FLUOROMETRIC DETERMINATION OF THE CONCENTRATIONS OF SUBSTANCES IN A SAMPLE AND ARRANGEMENT FOR IMPLEMENTING THIS METHOD

[75] Inventors: Otto S. Wolfbeis; Edmund Urbano, both of Graz, Austria

[73] Assignee: AVL AG, Schaffhausen, Switzerland

[21] Appl. No.: 617,818

[22] Filed: Jun. 6, 1984

[30] Foreign Application Priority Data

Jun. 8, 1983 [AT] Austria .................................. 2098/83

[51] Int. Cl.⁴ ............................................. G01T 21/64
[52] U.S. Cl. ................................ 250/459.1; 250/458.1
[58] Field of Search .................. 250/365, 459.1, 461.1, 250/361 R, 458.1, 461.2, 372, 373, 302, 364; 356/317, 318, 417; 436/172

[56] References Cited

U.S. PATENT DOCUMENTS 3,612,866 10/1971 Stevens .............................. 250/373
3,725,658 4/1973 Stanley et al. ..................... 250/302

FOREIGN PATENT DOCUMENTS 2508637 11/1979 Fed. Rep. of Germany .

OTHER PUBLICATIONS

Hurtubise, "Selective Fluorescence Quenching and Determination of Phenolic Antioxidants", Anal. Chem. 48 (14), Dec. 1976, pp. 2092-2095.

Primary Examiner—Carolyn E. Fields
Attorney, Agent, or Firm—Watson, Cole, Grindle & Watson

[57] ABSTRACT

For the simultaneous measurement of the concentrations of several substances a number of fluorescence measurements corresponding to the number of substances to be tested are performed using at least one fluorescent indicator which is non-specific relative to at least one of the substances to be tested, each fluorescent indicator having different quenching constants with regard to the individual substances quenching its intensities.

From the known, unquenched fluorescence intensities of the fluorescent indicators employed, the quenched fluorescence intensities obtained by measuring, and from the quenching constants that are known, or rather, have been determined beforehand by graphical methods or calculation, the concentrations and/or concentration ratios of the individual substances are obtained.

18 Claims, 4 Drawing Figures

METHOD FOR FLUOROMETRIC DETERMINATION OF THE CONCENTRATIONS OF SUBSTANCES IN A SAMPLE AND ARRANGEMENT FOR IMPLEMENTING THIS METHOD

BACKGROUND OF THE INVENTION

This invention relates to a method for the fluorometric determination of the concentrations of substances, such as gases or liquids, contained in a sample, using fluorescent indicators whose fluorescence intensity is reduced or quenched by the substances to be tested. The invention further relates to an apparatus for implementing this method, the apparatus including a sample chamber provided with fluorescent indicators in which the sample containing the test substances is placed, the fluorescence intensity of the fluorescent radiation which is excited in the above indicators by a light source being diminishable or quenchable by the substances to be tested.

An object of the present invention is to design a method and an apparatus for the fluorometric determination of one or more substance concentrations by means of fluorescent indicators which need no longer be specific to the test substances, thus permitting different substances to be measured simultaneously using fluorescent indicators that may be chosen arbitrarily. A main object is the determination of concentration ratios or other ratios of interest between two given concentrations.

DESCRIPTION OF THE PRIOR ART

It is known that the ability of certain dyes to fluoresce can be reduced by the addition of certain substances, so-called quenchers. The relation between the concentration of the so-called quencher and reduction in fluorescence intensity, according to Stern and Volmer, is as follows:

$$\frac{F^o}{F} - 1 = k[Q] \tag{1}$$

In this context, $F^o$ denotes the fluorescence intensity of a fluorescent indicator in the absence of a quencher, $F$ the fluorescence intensity of a fluorescent indicator in the presence of a quencher, $k$ the so-called quenching constant specific to each pair of quencher/fluorescence indicator, $[Q]$ the concentration of the quenching substance or quencher.

Since $F^o$ and $k$ are constants for the respective fluorescent indicators or indicator substances used, the quencher concentration may be inferred from the measurement of $F$. If $F^o$ and $k$ are unknown, they are eliminated by performing measurements and by preparing calibration lines or curves, $F$ being plotted against $[Q]$, and $F^o$ and $k$ being determined graphically, for instance.

This analytical method has found various applications. In U.S. Pat. No. 3,612,866, for instance, there is shown a method for measuring oxygen concentrations in various samples, e.g. blood. The method is based on the ability of oxygen as a quencher to reduce the fluorescence intensity of certain aromatic hydrocarbons, e.g. pyrene, in accordance with equation (1). In the journal "Biochemistry" (vol. 9, p.464, 1970) a method is described for tracing the local oxygen concentration by observing the quenching of fluorescence by means of pyrene butyric acid. In "Zeitschrift für Analytische Chemie" (vol. 314, p. 577, 1983) a method is described for determining with great accuracy the concentration of halide ions by using certain heterocyclic fluorescent indicators and observing the ensuing quenching of fluorescence. German Laid Open print No. 25 08 637 shows a method for the optical measurement of blood gases which is also based on the principle of fluorescence quenching. Other analytical methods for determining the concentrations of certain substances by means of fluorescence quenching are described in the journal "Analyst" (vol. 107, p. 465, 1982).

All of the above methods are characterized by a common disadvantage: The fluorescent indicators or indicator substances must be specific to the substance to be measured, i.e., they must only respond to this particular sample substance. In practice, most fluorescent indicators will respond to more than one substance, however, or rather, they will be quenched by a number of substances.

SUMMARY OF THE INVENTION

The method described by the present invention enables for the first time simultaneous fluorometric determination of several analytical quantities or substance concentrations, even if the indicator is no longer a specific one—, or determination of one single concentration despite the presence of interfering or quenching substances. According to the present invention this is achieved—above all, if the concentrations of two or more substances are to be determined simultaneously—by performing several measurements of fluorescence intensity on the sample containing these substances, the number of measurements corresponding to the number of substance concentrations to be determined, using at least one fluorescent indicator which is non-specific relative to at least one of the substances to be measured or which may be quenched by more than one of the substances, and which has different quenching constants with regard to the individual substances ("quenchers") quenching its intensities, and by obtaining the concentrations of the individual substances and/or the ratios of substance concentrations from the known, unquenched fluorescence intensities of the fluorescent indicators employed, and from the quenched or reduced fluorescence intensities obtained by measuring, and the various quenching constants which are known or have been obtained beforehand by graphical or computational methods.

The invention is based on the finding that equation (1) must be extended in order to reflect mathematically the influence of several quenchers, by adding more terms representing the influence of additional quenchers, i.e., additional substances to be measured. There results an equation for the case of two quenchers (2), and a general equation (3) for the instance of several quenchers or test substances quenching non-specific fluorescence indicators $$\frac{F^o}{F} - 1 = k_1[Q_1] + k_2[Q_2] \tag{2}$$

$$\frac{F^o}{F} - 1 = k_1[Q_1] + \ldots k_n[Q_n] \tag{3}$$

As equation (2) has two unknowns and equation (3) several unknowns, i.e., the various substance or quencher concentrations [Q], two or more independent measured values are required for solution; in the general case n measured values. They are obtained by measuring the fluorescence intensity F of two different fluorescent indicators quenched by the substances to be measured.

If an indicator A is used, a measured signal $$\frac{F_A^o}{F_A} - 1 = {}^1k_A[Q_1] + {}^2k_A[Q_2] \qquad (4)$$

will be obtained.

In equation (4), $F_A^o$ is the fluorescence intensity of indicator A in the absence of quenchers or the substances to be measured;

$F_A$ is the fluorescence intensity in the presence of quenchers or the substances to be measured;

${}^1k_A$ is the quenching constant of indicator A given quencher $Q_1$;

${}^2k_A$ is the quenching constant of indicator A given quencher $Q_2$;

$[Q_1]$ and $[Q_2]$ are the concentrations of the two quenchers.

If indicator B is used, the equation reads:

$$\frac{F_B^o}{F_B} - 1 = {}^1k_B[Q_1] + {}^2k_B[Q_2] \qquad (5)$$

$F_B^o$ is the fluorescence intensity of indicator B in the absence of quenchers;

$F_B$ is the fluorescence intensity in the presence of quenchers;

${}^1k_B$ is the quenching constant of indicator B given quencher $Q_1$;

${}^2k_B$ is the quenching constant of indicator B given quencher $Q_2$;

$[Q_1]$ and $[Q_2]$ are the concentrations of the two quenchers.

If, for the sake of simplicity, $\alpha$ is substituted for $$\frac{F_A^o}{F_A} - 1,$$

and $\beta$ is substituted for $$\frac{F_B^o}{F_B} - 1,$$

and if $[Q_2]$ calculated from equation (4) is put into equation (5), the following expression will result:

$$[Q_1] = \frac{(\alpha \cdot {}^2k_B - \beta \cdot {}^2k_A)}{({}^1k_A \cdot {}^2k_B - {}^2k_A \cdot {}^1k_B)} \qquad (6)$$

while for $[Q_2]$ one obtains:

$$[Q_2] = \frac{(\beta \cdot {}^1k_A - \alpha \cdot {}^1k_B)}{({}^1k_A \cdot {}^2k_B - {}^2k_A \cdot {}^1k_B)} \qquad (7)$$

${}^1k_A$, ${}^2k_A$, ${}^1k_B$ and ${}^2k_B$ are constant quantities that are known or have already been obtained. $\alpha$ and $\beta$ are variable quantities resulting from the values measured for the quenched intensities $F_A$ or $F_B$. From equations (6) and (7) the concentrations of the test substances or quenchers $Q_1$, $Q_2$ may now be obtained.

If three substances or quenchers are to be determined, three fluorescent indicators are necessary, and three quantities $\alpha$, $\beta$ and $\gamma$ must be measured, which are defined as follows:

$$\alpha = \frac{F_A^o}{F_A} - 1;\ \beta = \frac{F_B^o}{F_B} - 1;\ \gamma = \frac{F_C^o}{F_C} - 1 \qquad (8)$$

Using equation (3) this will result in three equations with nine quenching constants:

$$\alpha = {}^1k_A \cdot [Q_1] + {}^2k_A \cdot [Q_2] + {}^3k_A \cdot [Q_3]$$
$$\beta = {}^1k_B \cdot [Q_1] + {}^2k_B \cdot [Q_2] + {}^3k_B \cdot [Q_3] \qquad (9)$$
$$\gamma = {}^1k_C \cdot [Q_1] + {}^2k_C \cdot [Q_2] + {}^3k_C \cdot [Q_3]$$

In matrix notation, this system of equations may be written as $$\begin{pmatrix} \alpha \\ \beta \\ \gamma \end{pmatrix} = \begin{pmatrix} {}^1k_A & {}^2k_A & {}^3k_A \\ {}^1k_B & {}^2k_B & {}^3k_B \\ {}^1k_C & {}^2k_C & {}^3k_C \end{pmatrix} \cdot \begin{pmatrix} [Q_1] \\ [Q_2] \\ [Q_3] \end{pmatrix} \qquad (10)$$

and may be solved with the use of a suitable pocket calculator.

For determination of n unknown concentrations, n independent equations are set up in the same manner, and n values have to be measured for the quenched fluorescence intensities $F_n$.

The advantage of this method is that it will make it possible for the first time to determine fluorometrically, for instance by means of two non-specific fluorescent indicators, two unknown substance concentrations, provided that each of the two substances will quench both fluorescent indicators.

It will also be possible to determine only the concentration of one substance in the presence of an irrelevant or an interfering substance acting as a quencher. In this instance again two measured values will be required, i.e., the quenched fluorescence intensities of the two fluorescent indicators, the values for the substance concentrations being calculated as described above, except for the fact that the quenched intensity of the interfering substance is needed as an auxiliary variable and that the actual concentration of the interfering substance need not necessarily be calculated. In this case the method described by the present invention will be used for discriminating the desired substance concentration from that of an interfering substance, and will be characterized in that, for determining the concentration of at least one substance in the presence of at least one other, irrelevant or interfering, substance quenching the fluorescence intensity (-ies) of the fluorescent indicator(s) responding to the substance(s) to be measured, the concentration(s) of the other, interfering substance(s) is (are) determined just as the concentration(s) of the substance(s) to be measured, and is (are) used for determining the concentration of the substance to be measured.

Similarly, any effects of n interfering or irrelevant substances may be eliminated by n measured values for quenched fluorescence intensities of these unwanted substances, which, together with the quenched fluorescence intensity of the substance to be measured, are put into n+1 equations. The equations can only be solved if the quenching constants k are different for all indicator/quencher combinations. The number of concentrations to be determined thus is identical with the nunber of quenched intensities of relevant and interfering substances necessary for solving the equations.

Equations (6) and (7) are greatly simplified by using at least one indicator specific to a substance. In this case one of the quenching constants will equal zero, and the fraction will consist of three terms only.

If only the ratio of two quencher concentrations is to be determined, equation (11) will apply which results from combining equations (6) and (7):

$$\frac{[Q_1]}{[Q_2]} = \frac{\alpha \cdot {}^2k_B - \beta \cdot {}^2k_A}{\beta \cdot {}^1k_A - \alpha \cdot {}^1k_B} \quad (11)$$

It may be possible that fluorescent indicators are used which are made from the same fluorescent indicator substance, but that this substance is maintained in different indicator environments, for instance in different solutions or bonds and that these fluorescent indicators have different quenching constants in the different indicator environments for the substance or quencher to be measured. Fluorescent indicators or indicator substances which are embedded in different environments and therefore have different quenching constants varying with the respective substances used should be regarded as different fluorescent indicators which are to be used independently of each other for the method under discussion.

Depending on the individual application, fluorescent indicators may be used which are in the same phase or contained in the same sample substance as the substances to be tested. it may be of advantage if the substances to be tested are allowed to diffuse into the indicator phase in case the fluorescent indicators are in a different phase or are separated form the test substances and/or if the fluorescent indicators are added simultaneously to the test substances, or rather to the sample containing these substances, or are distributed over several substance solutions or indicator membranes. It will also be possible to have fluorescent indicators which are in the same phase or same sample material as the substances to be tested.

The choice of phase, i.e., whether the fluorescent indicator is to be in the same phase as the test substance or in a different one, will depend on the particular requirements. If the indicator is in the same phase, a high measurement sensitivity may be achieved as the quenchers will be able to reach the indicator practically unimpeded. On the other hand, quenching specificity will be low since virtually all quenchers present in the solution will become active. If the indicator is in a different phase this will usually reduce measurement sensitivity as the quencher will first have to diffuse into the other phase where its quenching efficiency will be lower, at least in most practical cases (e.g. in a polymer), which will result in smaller signal changes and thus in lower sensitivity and accuracy. On the other hand, quenching specificity will improve markedly since only substances able to diffuse into the second phase may act as quenchers, i.e., mostly gases or small molecules only.

According to the invention, an apparatus as mentioned in the beginning for implementing the method described is characterized in that the sample chamber is provided with a number of fluorescent indicators corresponding to the number of substance concentrations to be determined simultaneously, and that at least one of these fluorescent indicators will respond non-specifically to at least one of the substances to be measured, or will be quenchable by more than one substance, and that the quenching constants of this concentration indicator will vary for each of its quenchers, and that the signals of the individual fluorescent indicators corresponding to the reduced or quenched fluorescence intensities will be passed to an evaluation unit, possibly via amplifiers, for determining the concentrations and/or the concentration ratio of the indivdual substances to be measured. This arrangement will permit the concentrations or concentration ratios of substances to be determined with the use of non-specific fluorescent indicators, even if these substances are mixed with irrelevant interfering substances.

In a preferred form of the invention the evaluation unit is provided with a divider unit into which are fed the values measured for the unquenched fluorescence intensity of the individual fluorescent indicators as well as the values for the indivdual fluorescence intensities obtained from the fluorescent indicators, possibly after subtraction of a constant value corresponding to a straylight component, and the resulting quotient is fed into a subtraction unit contained in the evaluation unit where the value of 1 may be subtracted from this quotient, and the above evaluation unit is provided with a calculator unit for calculating the concentrations and/or concentration ratios of the individual substances.

It will be convenient if at least some of the fluorescent indicators contain an indicator substance which is maintained in a different environment, solution or bond, for each individual indicator, and has different quenching constants relative to its quenchers.

Depending on the respective requirements, it may be of advantage if the fluorescent indicators or substances are distributed over several substance solutions or indicator membranes, and/or if reaction spaces are provided between the sample chamber and the fluorescent indicators, in which quenchable substances can be transformed into nonquenchable substances, or vice versa, by chemical reaction, and/or if the indicator elements or fluorescent indicators are placed in the tip of a test probe that may be dipped into the sample containing the substances. Apart from the possibility of using the sample chamber as a reaction space at the same time, a separate reaction space may be provided behind the sample chamber.

In order to eliminate intensity variations of the light source it will be convenient for evaluation purposes to provide the fluorescent indicators with a reference light measuring cell or a reference indicator which may be connected to the calculator unit via an amplifier.

DESCRIPTION OF THE DRAWINGS

The following is a more detailed description of the invention, as illustrated by the enclosed drawings, in which.

DETAILED DESCRIPTION OF THE PREFERRED EMBODIMENTS

Figure 1:
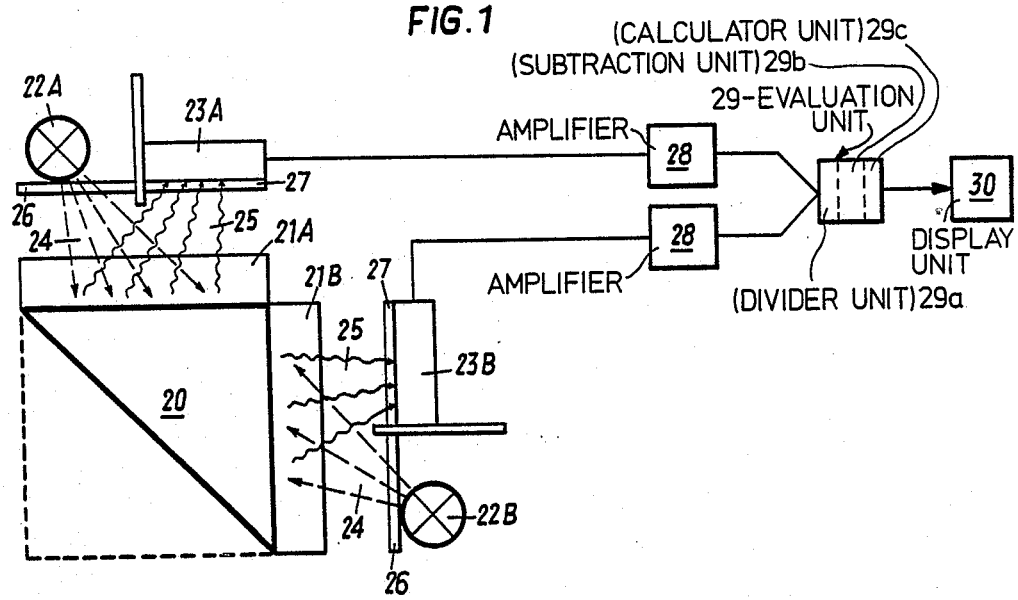
FIGS. 1-3 show various measuring arrangements.
Figure 2:
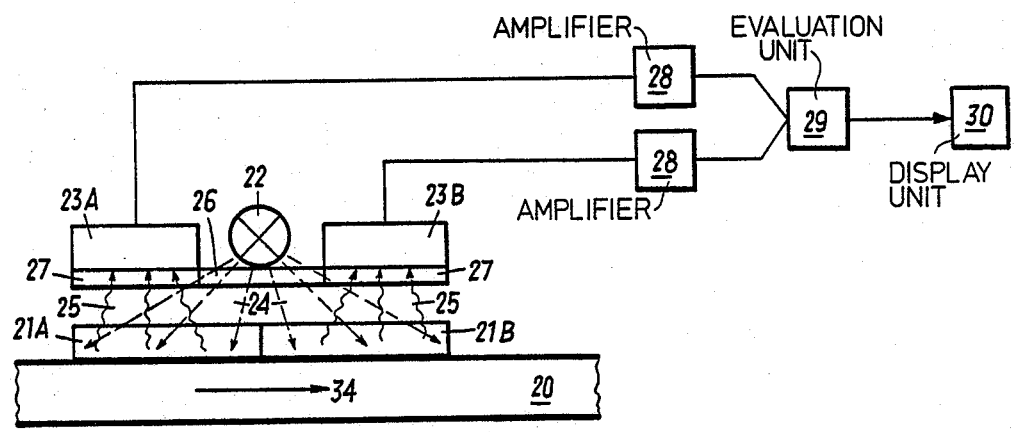

FIGS. 1 and 2 show simple arrangements for implementing the method described by the present invention for the common case of two diffusible substances in liquid or gaseous samples. On the outside of a sample chamber 20 fluorescent indicators or sensors 21A and 21B are provided. In the fluorescent indicators 21A and 21B light sources 22A and 22B will generate fluorescences whose intensities are measured by photodetectors 23A, 23B. In the absence of quenchers or the substances to be tested the fluorescence intensity F° will be particularly high; the measured values will correspond to the quantitites $F_A°$, $F_B20$ in equation (2). For measurement purposes the sample containing the test substances is introduced into, or passed through, the sample chamber 20. From sample chamber 20 quencher substances may diffuse into the fluorescent indicators 21A, 21B (e.g., oxygen, sulphur dioxide, halothane, etc.). In the above indicators these quenchers will cause a reversible reduction of the fluorescence intensity to the value F (equations (2), or (4) and (5) ). If the fluorescence intensity $F_A$, $F_B$ of the indicators 21A, 21B is measured, the concentrations of the quenchers may be calculated from the known values of $F_A°$ and $F_B°$ and of the quenching constants k. For better discrimination of the excitation light 24 and the fluorescent light 25, optical filters or interference filters 26, 27 may be introduced into the radiation path.

The sample chambers 20 may be designed as single sample measurement chambers or as flow measurement cells. The method and arrangement described by the present invention may be used for measuring both single samples and continous sample streams.

Light sources may include thermoelectric, electronic, laser- or LED-type devices operating either in a continous or in a pulsed mode.

The fluorescent indicators used in this context usually consist of solutions of quencher-sensitive materials or of indicator substances in thin membranes made of polymer materials, containing plasticizers, if required. As an alternative, fluorescent indicator materials or substances may be covalently bonded to a carrier material.

Suitable indicators are fluorescent indicators or indicator substances, possibly in differing environments, whose fluorescence is quenched by extraneous substances. These indicators should be highly fluorescent and stable. The following indicator/quencher combinations are given as examples:
pyrenbutyric acid —oxygen
chlorophyll —sulphur dioxide
quinine sulphate —chloride ion
acridine sulphate —bromide ion
indole —$H_2O_2$
benzo(ghi)perylene —haloethane The photodetectors 23A, 23B are used for measuring the intensity of the fluorescent light which will depend on the quencher concentration. For light measurement or detection photoelectric cells, photoamplifiers or photodiodes may be used. The measurement signal obtained usually is amplified in an amplifier unit 28 before it is fed into an analog or digital calculator or evaluation unit 29 and a display unit 30. In the calculator unit 29, which can include a divider unit 29a, a subtraction unit 29b and a calculator unit 29c, the concentrations of the substances to be investigated are determined by means of the above equations.

Figure 3:
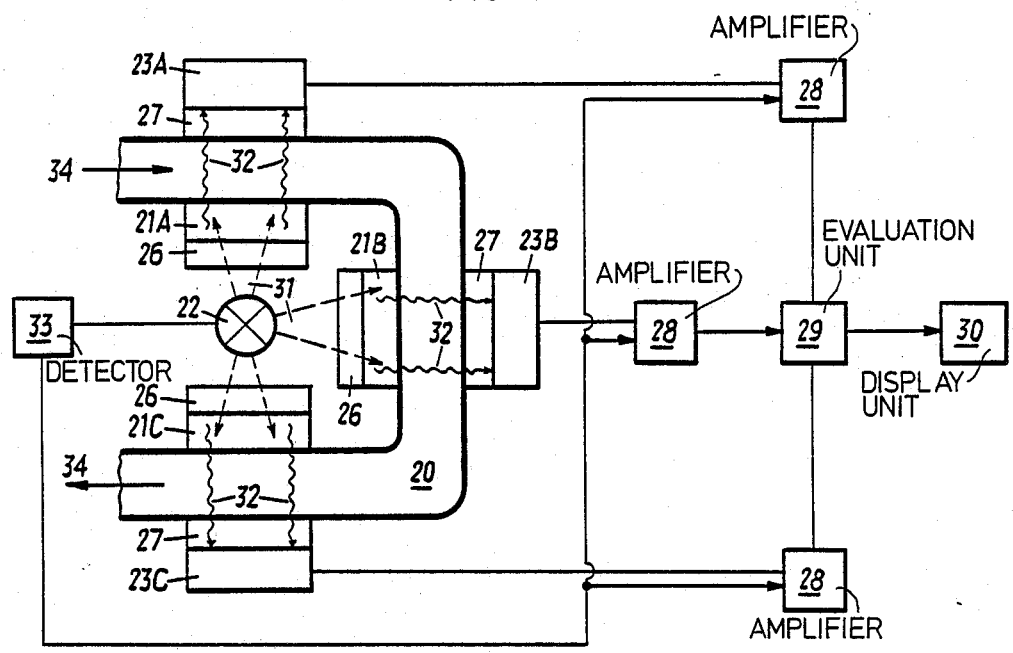

FIG. 3 presents a schematical view showing the continuous measurement of three substances in optically transparent material streams, e.g., of gases or liquids. The test substances will flow in the direction of arrows 34 through a sample chamber 20 formed by an U-shaped pipe, passing three fluorescent indicators 21A, 21B, 21C, which are excited to fluorescence by the light 31 of a light source 22 that may have passed a filter 26. The fluorescent light 32 emitted by the indicators 21A, 21B, 21C is measured by detectors 23A, 23B, 23C, possibly after passage of light filtering devices 27. The signals received are amplified in amplifiers 28 and are evaluated by means of an evaluation unit 29 according to equations (8), (9) and (10). They may then be displayed in the display unit 30 in an analog or digital manner, or they may be printed out. The ratio of quencher concentrations is determined with the use of equation (10).

It should be noted that it may often be practical to subtract a constant quantity $F_s$ from the signal measured or from the measured fluorescence intensity F in order to arrive at the measurement signal proper. The quantity $F_s$ will help to take into account interferences from the fluorescent light or stray light entering the fluorescence detection system on account of light scattering. The stray light component $F_s$ is determined, firstly, by modifying the Stern-Volmer-equation such that the straylight component $F_s$ is taken into account:

Stern-Volmer:

$$\frac{F^o}{F} - 1 = k\,[Q]$$

$$F^o = I^o - F_s$$
$$F = I - F_s$$

$I°$, $I$ : detected light intensities (fluorescent light + stray light)

The result is:

$$\frac{I^o - F_s}{I - F_s} - 1 = k\,[Q]$$

A three-point calibration will result in three calibration values:

$$[Q]_o = 0 \longrightarrow I_o$$

$$[Q]_1 \longrightarrow I_1$$

$$[Q]_2 \longrightarrow I_2,$$

leaving two equations with two unknowns (k, $F_s$):

$$\frac{I_o - F_s}{I_1 - F_s} - 1 = k\,[Q]_1$$

$$\frac{I_o - F_s}{I_2 - F_s} - 1 = k\,[Q]_2$$

In this manner straylight components $F_s$ and quenching constants for any sensor (any quencher) may be determined by calibration.

The description of these measuring arrangements should help to explain the principle of measurement. In accordance with the special requirements of any particular application the apparatus may vary and other components may be used. It may become necessary, for example, to use optical fibres for the transport of light from the light source to the fluorescent indicators, and from the indicators to the photodetectors. Besides, it is possible to add so-called ion carriers to the indicator membranes in order to facilitate diffusion of the quenchers through the membranes and into the indicators, or to enhance selectivity.

There are several ways of obtaining the desired measurement values or concentrations. If two values are required, which is frequently the case, (a) the fluorescence intensities $F_A$ and $F_B$ of two fluorescent indicators containing different indicator substances may be measured in the presence of the quenchers or the substances to be determined, upon which the concentrations of the quenchers $Q_1$ and $Q_2$ can be obtained by using equations (6) and (7), or by graphical methods;

(b) the fluorescence intensities $F_A$ and $F_A'$ of two fluorescent indicators may be measured, containing the same indicator substance, but each in a different indicator environment, e.g., in different solvents or different polymer membranes. As the quenching constants k of an indicator substance will vary with the type of environment or solvent, the concentrations of two quenchers again may be obtained by means of equations (6) and (7), or by graphical methods. $F_B'$ should be substituted by $F_A'$.

The same will apply if more than two materials or indicator substances in more than two different environments or solutions are to be investigated. The methods of measurement covered by the invention may vary in type, setup and geometrical arrangement.

Interaction between fluorescent indicator or indicator substance and quencher may take place in a homogeneous solution, by combining solutions of the substance to be tested and the indicator (e.g., measurements in cuvettes, as discussed in the subsequent examples 1 and 2).

Interaction between fluorescent indicator and the substance to be tested may also take place by using indicators whose phase differs from that of the sample substance, and by letting the quencher substances diffuse from the sample containing the substances into the indicator or indicator substance (e.g., when determining gas concentrations by means of membrane-type sensors, as shown in FIGS. 1–3).

Fluorescent indicators which emit radiation permitting spectral discrimination may be embedded in one single solution or membrane, or they may be distributed over a number of solutions or membranes.

It is possible to place several membranes either one above the other or side by side. In order to improve selectivity the indicators or indicator elements may be covered by additional, permeation-selective membranes.

In another variant of the invention the indicator elements may be provided with reaction spaces in which quenching substances are transformed into nonquenching ones by means of chemical reactions, or, vice versa, non-quenching substances are made quenching, thus permitting an indirect measurement of non-quenching substances as well.

Fluorescent indicators in this context denote either indicator substances as such or indicator substances applied to carrier media.

Intensity fluctuations of the light source 22 may be eliminated by incorporating a reference light measuring cell 33 (FIG. 3) which will measure the intensity of the light source 22 and is connected to the amplifiers 28 in order to compensate fluctuations of the light source 22, or rather, to avoid their being interpreted as changes in fluorescence intensity. The present invention has a wide variety of applications, some of which are mentioned below. The examples given should not be taken to preclude other possible uses.

(a) Simultaneous measurement of oxygen and sulphur dioxide in industrial waste gases, or in measuring facilities for environmental pollution.
(b) Measurement of oxygen concentrations, e.g. in road tunnels, in the presence of interfering automobile exhaust gases ($SO_2$, $NO_x$).
(c) Simultaneous measurement of the quenchers oxygen and haloethane in anaesthetic gas during anaesthesia.
(d) Continuous measurement of chloride and sulphite in effluents.

Following is detailed explanation of the invention by means of examples demonstrating the accuracy of the method of measurement described by the invention.

EXAMPLE 1

Quantitative simultaneous fluorometric measurement of two quenchers (chloride and bromide) in homogeneous solution Underlying principle: The fluorescence intensity of the indicators quinine and acridine is quenched differently by bromide and chloride.

5.123 mg 1-chloro-2,4-dinitrobenzene (MW 202.56) and 4.602 mg benzalacetophenone dibromide (MW 368.08) were weighed together and burnt in an oxygen atmosphere. The combustion gases were absorbed in 5 ml of a 1-percent solution of hydrazine sulphate.

After absorption of the reaction gases the content of the flask was transferred to a 20-ml-graduated flask which was filled up without the addition of an indicator. 8 ml of this stock solution each were then pipetted into two 10-ml-graduated flasks. After the addition of 1 ml of a 2.0 $10^{-5}$ molar solution of quinine sulphate in 1 N sulphuric acid (indicator 1) to one of these flasks, and of 1 ml of a 1.0 $10^{-5}$ molar solution of acridine in 1 N sulphuric acid (indicator 2) to the other flask, both flasks were filled up with water to the 10-ml-mark. After preparation of two halide-free standard solutions their standard fluorescence intensities ($F_A^\circ$ and $F_B^\circ$) were set to 100. The relative $F_A$ value of the sample (indicator: quinine sulphate) was 76.1, and the $F_B$ value of the sample (indicator: acridine) also happened to be 76.1.

The quenching constants k necessary for evaluation of the test results had been determined beforehand and are listed in Table 1.

TABLE 1

| Quenching constants k for the indicators quinine sulphate and acridine (as used in the present example) in sulphuric acid. | | |
|---|---|---|
| Indicator | $Cl^-$ | $Br^-$ |
| Quinine sulphate in 0.1 N $H_2SO_4$ (A) | $^1k_A =$ 133.0 | $^1k_B =$ 177.5 |
| Acridine in 0.1 N $H_2SO_4$ (B) | $^2k_A =$ 9.5 | $^2k_B =$ 304.2 |

Results: The following test results were obtained:

$F_A° = F_B° = 100$ $F_A = F_B = 76.1$ $\alpha = (F_A°/F_A) - 1 = 0.31506$ $\beta = (F_B°/F_B) - 1 = 0.31506$ If the above quantities and the Stern-Volmer-constants k are entered into equations (6) and (7), the molar concentrations of the chloride and bromide quenchers are:

Cl$^-$ = 1.0296 mM = 0.9126 mg/25 ml total sample volume

Br$^-$ = 1.0036 mM = 2.0048 mg/25 ml total sample volume

The halide content in mg is obtained by multiplying the molar quencher concentrations of the samples with the molecular weight and the total sample volume in ml, and by dividing them by 1000.

If the measured value in mg/total sample volume is divided by the input in mg, and the result is multiplied by 100, the relative content of halides as a percentage will be obtained. For the present example this yields, with a total input of 9.9725 mg, for chloride 9.38%, versus a calculated 9.22%, and for bromide 20.61%, versus a calculated 20.55%.

EXAMPLE 2

Quantitative simultaneous fluorometric measurement of three quenchers (chloride, bromide, iodide) in homogeneous solution Underlying principle: The fluorescence of the indicators quinine, acridine and harman is quenched diffrently by chloride, bromide and iodide.

The simultaneous fluorometric measurement of three quenchers was tested by means of three potassium halide solutions. First of all, the quenching constants were determined and their additive combination into one overall quenching constant was checked. The results of this measurement are presented in Table 2.

TABLE 2

Ion specific quenching constants and overall quenching constants for halides which are simultaneously present in the solution.
Indicator: quinine sulphate in 0.1 N $H_2SO_4$.

| Overall halide concentration mM | halide | k$^a$ |
|---|---|---|
| 1 | KCl | 133 |
| 1 | KBr | 178 |
| 1 | KJ | 243 |
| 2 | KCl + KBr | 310 |
| 2 | KCl + KJ | 377 |
| 2 | KBr + KJ | 421 |
| 3 | KCl + KBr + KJ | 557 |

$^a$The overall quenching constants refer to identical concentrations of the quenchers present.

As is shown in Table 2, the overall quenching constants are additive combinations from the individually determined ion-specific constants. This proves that the contributions of the individual ions or substances to the quenching effect are independent of the presence of other quenchers.

For simultaneous measurement of the three halides, 1 ml each of a 1.00 10$^{-2}$ molar solution of KCl, KBr od KJ was pipetted into each of three 10-ml-graduated flasks. From the indicators quinine sulphate, acridine and harman, solutions in 1 N sulphuric acid were prepared, and 1 ml of the first of the three indicator solutions was added to the first flask, 1 ml of the second solution was added to the second flask, and 1 ml of the third solution was added to the third flask. After the graduated flasks had been filled up, the fluorescence intensity F of the samples relative to the fluorescence intensity F° of the respective standard solutions (1 ml indicator solution/10 ml water) was measured. Their standard fluorescence intensity F° was set to 100 and checked after each measurement. The quenching constants found for the individual indicators are presented in Table 3.

TABLE 3

Quenching constants for the simultaneous measurement of chloride, bromide and iodide in homogeneous aqueous solution.

| Indicator | Cl$^-$ | Br$^-$ | J$^-$ |
|---|---|---|---|
| Quinine sulphate in 0.1 N $H_2SO_4$ (A) | 133 ($^1k_A$) | 178 ($^2k_A$) | 243 ($^3k_A$) |
| Acridine in 0.1 N $H_2SO_4$ (B) | 9.5 ($^1k_B$) | 304.1 ($^2k_B$) | 396.7 ($^3k_B$) |
| Harman in 0.1 N $H_2SO_4$ (C) | 0.2 ($^1k_C$) | 9.4 ($^2k_C$) | 212.4 ($^3k_C$) |

The three values measured for the relative fluorescence intensities $F_A$, $F_B$, $F_C$ were:

$F_A = 64.3$, $F_B = 58.4$, $F_C = 81.8$ $F_A° = F_B° = F_C° = 100$ standard fluorescence intensities $\alpha = (F_A°/F_A) - 1 = 0.55521$ $\beta = (F_B°/F_B) - 1 = 0.71233$ $\gamma = (F_C°/F_C) - 1 = 0.22249$ Calculation according to equations (8) to (10) yields:
System determinant = 7759322.2
Determinant or co-determinant 1 = 7762.839
Determinant or co-determinant 2 = 7786.451
Determinant or co-determinant 3 = 7776.161

For calculation of the i-th unknown the i-th column of the system determinant was replaced by the left-hand side of equation (10). This yields the following concentrations of the halide solutions:

[Cl$^-$] = 1.000 mM
[Br$^-$] = 1.003 mM
[J$^-$] = 1.002 mM

The concentrations determined in this manner correspond closely to the input values (1.000 mM).

EXAMPLE 3

Simultaneous continuous measurement of oxygen and halothane in an anaesthetic gas Underlying principle: The fluorescence of certain aromatic hydrocarbons is quenched by oxygen and halothane (an anaesthetic gas with the symbol 2-bromine-2-chlorine-1,1,1-trifluoroethane).

Figure 4:
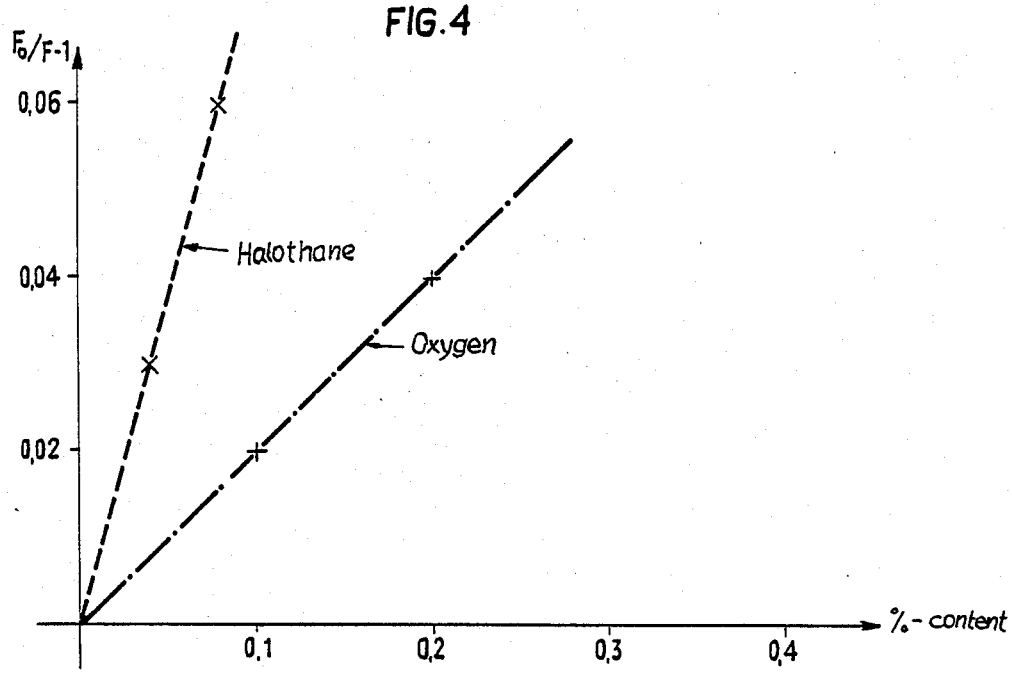
FIG. 4 presents a diagram for determining the quenching constants.

In a measuring arrangement as presented schematically and in a simplified form in FIG. 2, the quenching of fluorescence by means of a gas containing 20% oxygen and 4.4% halothane, was measured. The fluorescent indicators 21A and 21B contained solutions of decacyclene or benzo(ghi)perylene or heterocyclic compounds in cross-liked silicones or polyvinylchloride with a high plasticizer content. In preliminary tests—as shown in FIG. 4—the quenching constants $^1k_A$ (quenching of fluorescent indicator 21A by the first quencher $O_2$), $^2k_A$ (quenching of indicator 21B by halothane) $^1k_B$ (quenching of indicator 21B by $O_2$ and $^2k_B$ (quenching of indicator 21B by halothane) were determined by experiment, using equation (1). In FIG. 4, the $O_2$/halothane concentrations $[Q_1][Q_2]$ are indicated along the abscissa axis, and the quotient of standard and relative fluorescence intensity minus 1 is plotted along the ordinate axis. The gradients of the plotted lines correspond to the quenching constants of indicator 1 for $O_2$ or halothane.

The quenching constants of indicators 1 and 2 are listed in Table 4.

TABLE 4

Quenching constants of fluorescent indicators containing aromatic hydrocarbons, using oxygen and halothane as quenchers.

| Sensor 1 | $^1k_A = 0.202$ | $^2k_A = 0.811$ |
| Sensor 2 | $^1k_B = 0.771$ | $^2k_B = 0.643$ |

The following values were obtained:
$F_A°/F_A = 1.073$; therefore $\alpha = 0.073$;
$F_B°/F_B = 1.180$; therefore $\beta = 0.180$.

If $\alpha$, $\beta$ and the quenching constants of Table 4 are inserted in equations (6) and (7), the values obtained for the concentrations of $O_2 [Q_1]$ and halothane $[Q_2]$ will be 0.1999 and 0.043, respectively, corresponding to 19.99 and 4.3 percent, respectively. This is in excellent accordance with the actual values of the oxygen and halothane contents.

We claim:

1. A method for the fluorometric determination of the concentration of a number n of individual constituent substances contained in a sample by using fluorescent indicator substances, said method comprising
   (1) providing at least one fluorescent indicator substance which is non-specific relative to at least one of said individual constituent substances and which has different quenching constants with respect to said individual constituent substances, the unquenched fluorescence intensity and the different quenching constants of each fluorescent indicator substance with respect to each of said individual constituent substances being known,
   (2) associating said fluorescent indicator substances with a sample containing a number n of individual constituent substances,
   (3) taking a number n of quenched fluorescence intensity measurements of said sample, and
   (4) determining the concentrations of said individual constituent substances and the ratio of individual constituent substance concentrations in said sample using the known unquenched fluorescence intensities of each fluorescent indicator substance, the different quenching constants of each fluorescent indicator substance, and the measured quenched fluorescence intensities obtained in step (3).

2. A method according to claim 1, wherein said sample in step (2) contains at least one irrelevant or interfering substance which quenches the fluorescence intensity of the fluorescent indicator substance which responds to at least one associated individual constituent substance, and wherein in step (3) the fluorescence intensity of each fluorescent indicator substance responsive to each irrelevant or interfering substance is measured, and wherein such measurements are used in step (4) to determine the concentration of each associated individual constituent substance.

3. A method according to claim 1, including, prior to step (4), the step of measuring a straylight component in the quenched fluorescence intensity measurements taken in step (3), and wherein said measured straylight component is used in determining the concentrations of individual constituent substances and the ratio of individual constituent concentrations in step (4).

4. A method according to claim 1, wherein said fluorescent indicator substances are contained separately from said sample containing said individual constituent substances, and wherein in step (2) said individual constituent substances diffuse into contact with said fluorescent indicator substances.

5. A method according to claim 4, wherein said fluorescent indicator substances are contained in at least one solution.

6. A method according to claim 4, wherein said fluorescent indicator substances are contained in a phase which is different from that of said sample containing said individual constituent substances.

7. A method according to claim 4, wherein said fluorescent indicator substances are contained in at least one membrane material.

8. A method according to claim 1, wherein said fluorescent indicator substances are located on the end of a test probe and in step (2) are dipped into said sample containing said individual constituent substances.

9. An apparatus for the fluometric determination of the concentration of a number n of individual constituent substances contained in a sample, said apparatus comprising
   a sample chamber for containing a sample having a number n of individual constituent substances therein,
   means containing a number n of fluorescent indicator substances which are quenchable by said individual constituent substances, at least one of said fluorescent indicator substances responding non-specifically to at least one of said individual constituent substances, each fluorescent indicator substance having quenching constants which are different for each of said individual constituent substances,
   a light means for directing excitation light towards said means containing said fluorescent indicator substances and causing said fluorescent indicator substances to emit fluorescent radiation,
   a detector means for detecting the fluorescent radiation emitted by said fluorescent indicator substances, and
   an evaluation unit means connected to said detector means for determining the concentrations and the concentration ratios of said individual constituent substances.

10. The apparatus according to claim 9, wherein said evaluation unit means includes a divider unit into which are fed unquenched fluorescence intensity values of said fluorescent indicator substances and measured quenched fluorescence intensity values and in which quotient values are determined, a subtraction unit, and a calculator unit for calculating the concentrations and concentration ratios of said individual constituent substances.

11. The apparatus according to claim 9, wherein said means containing a number n of fluorescent indicator substances comprises at least two indicator chambers positioned adjacent said sample chamber.

12. The apparatus according to claim 11, including at least one said light means for directing excitation light towards said indicator chamber and a separate said detector means for detecting the fluorescent radiation emitted by the fluorescent indicator substances in each respective indicator chamber.

13. The apparatus according to claim 12, including light filter means positioned between each light means and each indicator chamber.

14. The apparatus according to claim 12, including light filter means positioned between each indicator chamber and each associated detector means.

15. The apparatus according to claim 9, including a reference light measuring cell for directly receiving excitation light from said light means, said reference light measuring cell being electrically connected to said evaluation unit means.

16. The apparatus according to claim 9, wherein said means containing a number n of fluorescent indicator substances comprises at least two membranes.

17. The apparatus according to claim 9, wherein said sample chamber is linearly elongated.

18. The apparatus according to claim 9, wherein said sample chamber is U-shaped.

* * * * *